United States Patent [19]

Pierce

[11] Patent Number: 5,317,759
[45] Date of Patent: Jun. 7, 1994

[54] SURGICAL GLOVE

[76] Inventor: William S. Pierce, 1201 Saradana Rd., Harrisburg, Pa. 17112

[21] Appl. No.: 8,826

[22] Filed: Jan. 25, 1993

Related U.S. Application Data

[63] Continuation of Ser. No. 676,557, Mar. 28, 1991.

[51] Int. Cl.$^5$ ............................................. A41D 19/00
[52] U.S. Cl. ......................................... 2/161.7; 2/168; 428/119
[58] Field of Search .................. 2/167, 168, 169, 163, 2/159, 161 R, 2, 2.5, 161.6, 161.7; 428/119, 166, 911; 128/842, 844

[56] References Cited

U.S. PATENT DOCUMENTS

| | | | |
|---|---|---|---|
| 2,702,906 | 3/1955 | Causse | 2/159 |
| 3,633,216 | 1/1972 | Schonholtz | 2/168 |
| 4,308,860 | 1/1982 | Sanders et al. | 15/227 X |
| 4,371,988 | 2/1983 | Berend | 2/167 |
| 4,696,065 | 9/1987 | Elenteny | 2/168 |
| 4,723,324 | 2/1988 | Lassiter | 2/161 R X |
| 4,742,578 | 5/1988 | Seid | 2/2.5 |
| 4,779,290 | 10/1988 | Welch et al. | 2/161 |
| 4,864,661 | 9/1989 | Gimbel | 2/167 |
| 4,901,372 | 2/1990 | Pierce | 2/167 |
| 4,935,260 | 6/1990 | Shlenker | 427/2 |
| 4,947,487 | 8/1990 | Saffer et al. | 2/167 |
| 5,020,162 | 6/1991 | Kersten et al. | 2/168 X |
| 5,024,852 | 6/1991 | Busnel et al. | 2/161 R X |

FOREIGN PATENT DOCUMENTS

| | | | |
|---|---|---|---|
| 654995 | 12/1937 | Fed. Rep. of Germany | 2/168 |
| 2332844 | 1/1975 | Fed. Rep. of Germany | 2/168 |
| 479502 | 4/1916 | France | 2/168 |
| 709641 | 8/1931 | France | 2/19 |

OTHER PUBLICATIONS

Gerberding et al Article: "Risk of Exposure of Surgical Personnel to Patients' Blood During Surgery at San Francisco General Hosp." Jun. 21, 1990, The New England Journal of Medicine.

Picha and Siedlak Article: "Ion-Beam Microtexturing of Biomaterials", Apr. 1984, Medical Device & Diagnostic Industry.

*Primary Examiner*—Clifford D. Crowder
*Assistant Examiner*—Amy B. Vanatta
*Attorney, Agent, or Firm*—Thomas Hooker

[57] ABSTRACT

A barrier surgical glove for protecting surgeons and health care workers from bacterial or viral infections, such as hepatitis B and autoimmune deficiency syndrome (AIDS). The glove includes an inner layer, an outer layer overlying the inner layer and a plurality of closely spaced pillars at the interface between the layers integral with one layer and extending toward the other layer. The pillars provide protection against needle sticks extending completely through the glove while permitting flexibility of the glove and tactile sense transmission through the thickness of the glove.

21 Claims, 2 Drawing Sheets

SURGICAL GLOVE

This is a continuation of copending application Ser. No. 07/676,557, filed on Mar. 28, 1991.

FIELD OF THE INVENTION

The invention relates to a barrier glove for protecting health care workers from patient contamination due to needle sticks without sacrificing flexibility and tactility.

DESCRIPTION OF THE PRIOR ART

Surgical gloves are conventionally worn by surgeons and health care workers performing medical procedures, typically in an operating room, where it is important to maintain sterility and to protect the wearer from possible contamination from the patient. Important advances have been made in the operating room environment to reduce the risk of contamination of the surgeon or health care worker because of exposure to the infections carried by the patient. These improvements include skin preparation, patient draping and personnel gloving. However, little improvement has occurred in operating room gloves during the past 100 years. There is now considerable evidence suggesting that glove punctures occur in as many as 40 percent of operative procedures as a result of suture needle sticks. Double gloving is helpful in reducing needle sticks but does not eliminate needle sticks.

During long surgical operations, particularly where prosthetic materials such as artificial hips or heart valves are implanted, bacteria or viruses carried by the health care worker may cross these glove puncture sites and contaminate the surgical wound, resulting in a life-threatening infection of the patient. Moreover, there are risks to the health care worker. Bacteria or virus present in the patient's blood may be transmitted to members of the surgical team through glove punctures. Both the virus causing hepatitis B and the virus causing autoimmune deficiency syndrome (AIDS) may be transmitted in this manner and may cause serious disease and even death. Accordingly, better methods are being sought to provide a relatively impenetrable barrier between the body fluids of the patient and those of the operative team.

SUMMARY OF THE INVENTION

The invention is a two-layer glove having a flexible tactile transmitting and puncture-resistant construction at high risk puncture sites in order to reduce the probability of a needle stick extending completely through the glove. The glove includes inner and outer glove layers overlying each other with a plurality of closely spaced pillars at the interface between the layers at high risk puncture sites. The pillars are integral with one layer and extend toward the other layer thereby increasing the thickness of the glove at the puncture site and providing a very nearly solid additional layer of glove material for resisting punctures. The additional thickness of the glove at the high risk sites provided by the pillars increases the force required to move a suture needle completely through the glove thereby decreasing the likelihood of a complete puncture of the glove. Also, the added thickness decreases the risk that a small curved suture needle entering the outside glove layer will track through the entire glove and form a complete puncture.

While the pillars increase the thickness of the glove they are independent of each other and retain the desired flexibility of the glove. The pillars transmit tactile forces through the glove and to the hand of the health care worker wearing the glove. In this way, the glove may be worn to provide protection while performing very delicate surgical procedures where fine suturing is required including suturing during gynecological and cardiac surgery and surgery involving implantation of prosthetic materials and members.

Other objects and features of the invention will become apparent as the description proceeds, especially when taken in conjunction with the accompanying drawings illustrating the invention, of which there are 2 sheets and 6 embodiments.

DESCRIPTION OF THE PREFERRED EMBODIMENTS

Surgical glove 10 includes continuous thin, flexible and puncture resistant inner and outer glove layers 12 and 14 each having the shape of a glove with the outer layer 14 overlying the inner layer 12. The layers may be formed of rubber or synthetic material used to manufacture surgical gloves including latex, polyurethane, silicone rubber and the like. The layers may have a thickness of about 0.008 inch. The layers may be adhered to each other or may be simply fitted one over the other and held together by the natural resiliency of the materials when the glove is worn. It may be desirable to secure the two glove layers together at the cuff only while allowing the remainder of the layers to overlie each other.

Figure 1:
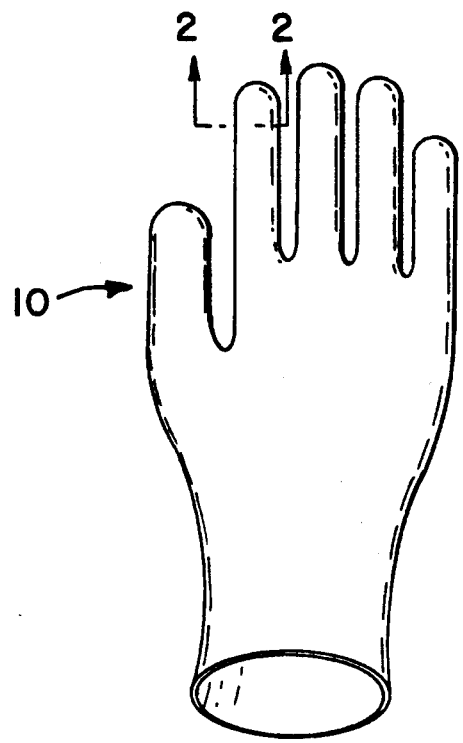
FIG. 1 is a view of a surgical glove according to the invention.
Figure 2:
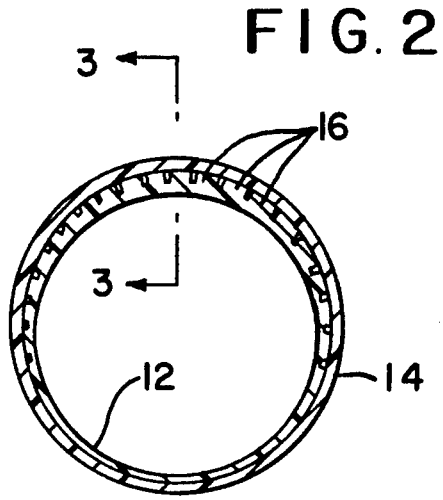
FIG. 2 is a sectional view taken along line 2—2 of FIG. 1 through a finger of the glove showing a puncture resistant section.

A plurality of closely spaced pillars 16 are provided between the layers at areas commonly associated with needle sticks during surgical procedures. The pillars resist puncture of the glove by suture needles of the type shown in FIG. 3. Pillars may be provided on the entire palm surface of the hand and fingers, possibly the back of the hand, the entire thumb and the lateral surfaces of the index finger. FIG. 2 is a sectional view through the tip of the index finger showing a plurality of the pillars 16 extending partially around the circumference of the finger.

The pillars are integral with the inner layer 12, have a width of about 0.008 inch, and extend upwardly from the layer a distance of approximately 0.008 inch so that the glove at the puncture resistant pillars has a total thickness of approximately 0.020 inch. The pillars have a center-to-center spacing of about 0.010 inch with approximately 0.002 inch wide slots between pillars. While the thickness of the glove at the pillars is greater than the thickness of a conventional surgical glove or a conventional double glove comprising two surgical gloves, one over the other, the thickness is not sufficiently great to inhibit movement of the hand or performance of surgical procedures.

Pillars 26 are freestanding above layer 12 and are spaced from each other so that the circumferentail sides of adjacent pillars are free of each other and permit relative vertical movement of adjacent pillars during the transmission of tactile forces through the thickness of the glove.

The pillars 16 are columnar in cross section and are separated from each other by narrow slots 18 to permit relative vertical movement of adjacent pillars. In this way, tactile sensation is readily transmitted across the thickness of the glove to the hand of the wearer so that the wearer retains an ability to feel or sense surgical procedures through the thickened and puncture resistant portions of the glove.

Figure 4:
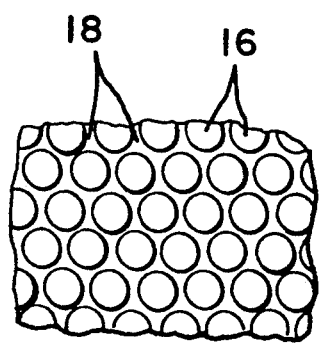
FIGS. 4, 5, 6 and 7 are top views of one layer of the glove showing different types of pillars.

FIGS. 4, 5, 6 and 7 are top views of an inner layer 12 showing different cross sectional configurations of the pillars. In FIG. 4 the pillars 16 have a circular cross section and are closely spaced together with each pillar extending into recesses between two adjacent pillars and the pillars aligned in 60-degree oriented rows. The narrow slots 18 between the pillars are not curved.

Figure 5:
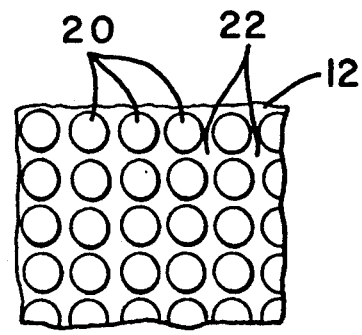

FIG. 5 illustrates cylindrical pillars 20 spaced in perpendicular rows at a slightly less dense arrangement than the arrangement of FIG. 4. Narrow slots 22 separate the pillars 20.

Figure 6:
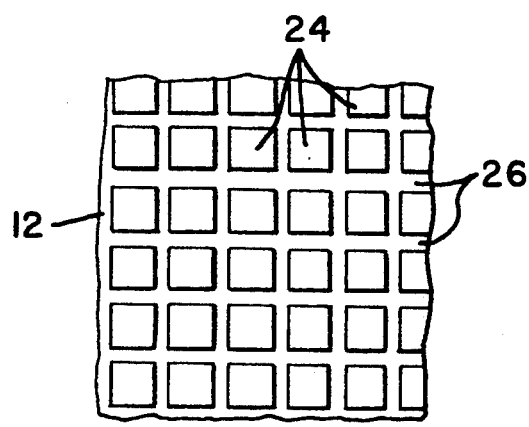

FIG. 6 shows square pillars 24 arranged in perpendicular rows and separated by narrow slots 26.

Figure 7:
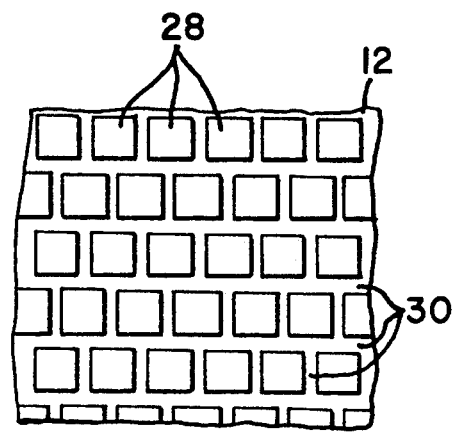

FIG. 7 shows square pillars 28 arranged in offset rows with the pillars separated by narrow slots 30.

Figure 8:
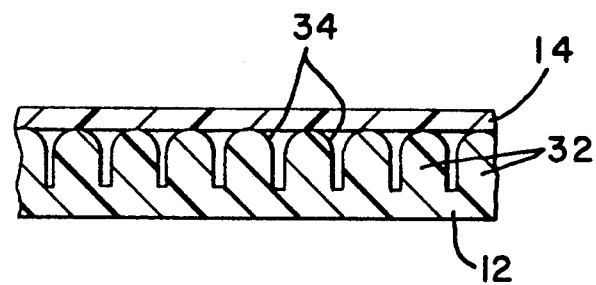
FIGS. 8 and 9 are views similar to FIG. 3 showing different shaped pillars.

The tops of the pillars may be flat as shown in FIGS. 3–7 or may be rounded as shown in FIG. 8 where pillars 32 have domed upper ends 34 engaging the outer layer 14 of the glove. The flattopped pillars provide additional material in the pillars and as a result provide a dense pillar layer in the glove with high puncture resistance.

Figure 9:
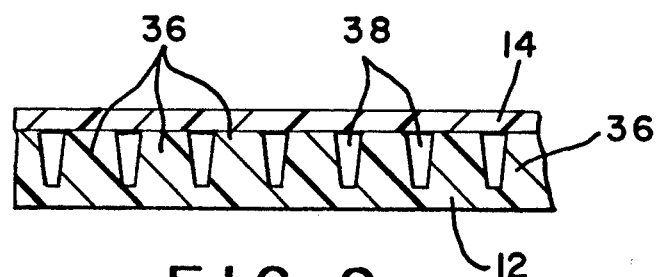

FIG. 9 illustrates a glove layer with tapered pillars 36 extending from the inner layer 12 to the outer layer 14. The pillars may have a rounded or square cross section with side walls that slope inwardly from the supporting layer 12 to the flat ends of the pillars. The ends may be rounded. Inwardly sloping pillar walls may facilitate manufacture of the pillars.

Figure 3:
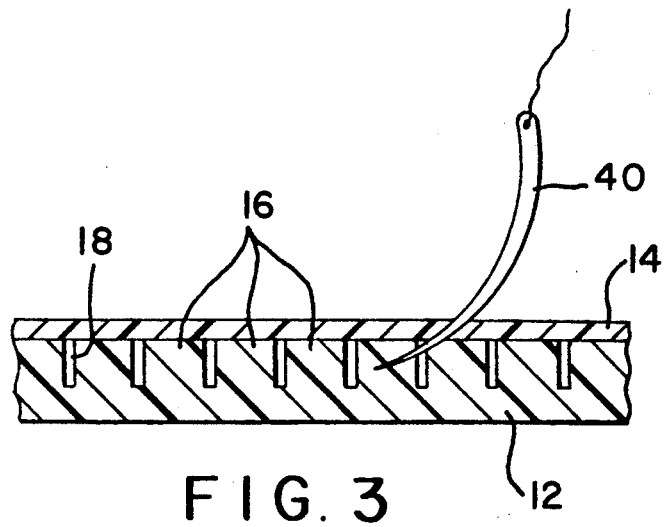
FIG. 3 is a sectional view along line 3—3 of FIG. 2 through a puncture resistant section of the glove showing a partial puncture by a suture needle.

The closely spaced individual pillars retain the flexibility and tactile force transmission of the glove while providing an increased thickness of glove material to resist needle sticks as shown in FIG. 3. The force required to puncture the glove is directly proportional to the amount of gloving material the needle must puncture. As shown in FIG. 3 the curvature of suture needle 40 tends to lead the needle along a curved path during entry of the glove. The increased thickness of the glove provided by the pillars increases the likelihood that a suture needle entering the glove will follow a curved path leading the tip up away from the hand of the wearer without complete puncture. The length of the curved path and the force required to continue the relatively long puncture may be sufficiently great to alert the wearer to a partial puncture and permit the wearer to release the needle prior to the needle piercing entire thickness of the three layer glove.

The drawings illustrate surgical gloves with pillars integral with and extending outwardly of the inner glove layer 12. Alternatively, the pillars may be formed on the inner surface of the outer layer and extend inwardly to engage the inner layer. A separate pillar layer may be provided. The pillars increase the effective thickness of the glove at areas where there is a high risk of needle sticks without decreasing the flexibility of the glove and permitting direct transmission of tactile sensations through the thickness of the glove.

The pillars are preferably closely spaced to each other with minimum width slots separating the pillars. In this way, the pillars nearly completely fill the space between the inner and outer layers 12 and 14 and provide a dense body of material resisting punctures or needle sticks.

Curved or non-linear slots between the pillars reduce the possibility that a suture needle puncturing the outer layer can extend freely through a slot without resistance and then more easily pierce the inner layer. Thus, the arrangement of cylindrical pillars shown in FIG. 4 with curved slots between the pillars provides a high degree of puncture-resistance. The pillar arrangement of FIG. 7 provides an increased degree of stick resistance for gloves using square pillars.

The glove layer carrying the pillars may be formed by a molding operation using a mold having the shape of a hand with a plurality of very closely spaced holes formed in the mold at the pillar sites on the hand. The holes conform in shape to the shape of the pillars. If desired, holes may be provided on the entire surface of the mold to provide pillars on the entire surface of the formed layer. The holes may be formed by laser-drilling or other conventional means.

The layer carrying the pillars is formed by dipping the mold into a liquid solution of glove material to form the continuous layer having the shape of the glove with integral pillars extending into the closely spaced holes in the mold. After the glove material on the mold cures the pillar layer is stripped from the mold, commonly by inverting the layer and peeling the layer from the wrist area past the finger area and off the mold. In this way, an inner glove layer 12 is formed with pillars extending outwardly as illustrated. Glove 10 is be completed by fitting a suitably dimensioned outer glove layer 14 over the inner layer 12 and, if desired, adhering the layers to each other as previously described.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A barrier surgical glove including inner and outer glove layers each formed from flexible puncture resistant material with the outer glove layer overlying the inner glove layer, and a plurality of closely spaced independent pillars located in the interface between the layers, said pillars being integral with one layer and extending toward and contacting the other layer, each pillar having a circumferential sidewall extending completely around the pillar, the sidewalls of adjacent pillars being free of each other to permit relative movement of adjacent pillars during transmission of tactile forces through the thickness of the glove.

2. A glove as in claim 1 including narrow slots between adjacent pillars.

3. A glove as in claim 1 wherein the pillars have a height approximately equal to the thickness of a layer.

4. A glove as in claim 1 wherein the thickness of the layers is approximately 0.008 inch, the pillars have a height of 0.008 inch and a center-to-center spacing of about 0.010 inch.

5. A glove as in claim 4 wherein the pillars have a width of approximately 0.008 inch.

6. A glove as in claim 2 wherein the slots between the pillars are non-linear.

7. A glove as in claim 1 wherein the pillars are generally cylindrical.

8. A glove as in claim 1 wherein the sidewalls of adjacent pillars are spaced apart from each other to define slots separating adjacent pillars.

9. A glove as in claim 8 wherein said slots extend past a plurality of spaced pillars and are non-linear.

10. A protective covering as in claim 8 wherein the slots extend non-linearly across the first layer.

11. A barrier protective coating including a first layer formed from a thin flexible material, a plurality of closely spaced independent and free-standing pillars joined to the first layer, said pillars extending away from the first layer to pillar ends located a distance outwardly of the first layer, the pillars having circumferential sides surrounding the pillars and extending along the pillars from the first layer to the pillar ends, the sides of individual pillars being unconnected to the sides of adjacent pillars to permit movement of individual pillars toward the first layer without movement of adjacent pillars for transmission of tactile sensation through the thickness of the covering; and a second layer formed from a thin flexible material overlying the fist layer and engaging the ends of the pillars so that the pillars are located between the layers.

12. A barrier protective covering as in claim 11 wherein said first layer and pillars are integral.

13. A barrier protective covering as in claim 11 wherein the sides of adjacent pillars are spaced a distance apart from each other.

14. A protective covering as in claim 11 wherein the pillars are generally cylindrical.

15. A protective covering as in claim 11 wherein the pillars are generally rectangular.

16. A protective covering as in claim 11 wherein the ends of the pillars are flat.

17. A protective covering as in claim 11 wherein the ends of the pillars are rounded.

18. A protective covering as in claim 11 wherein said pillars have a center-to-center spacing of about 0.010 inch.

19. A protective covering as in claim 11 comprising a glove, said inner layer having the shape of the glove, said outer layer having the shape of a glove and said pillars are located at a high puncture risk site on the glove.

20. A glove as in claim 19 including slots between adjacent pillars, said slots being non-linear.

21. A protective covering as in claim 19 wherein said pillars have a width and height of approximately 0.008 inch.

* * * * *

UNITED STATES PATENT AND TRADEMARK OFFICE
CERTIFICATE OF CORRECTION

PATENT NO. : 5,317,759
DATED : June 7, 1994
INVENTOR(S) : William S. Pierce

It is certified that error appears in the above-identified patent and that said Letters Patent is hereby corrected as shown below:

Column 1, line 5, change "No. 07/676/557" to --No. 07/676,557--.

Column 3, line 3, change "pillars 26" to --pillars 16--.

Claim 10, line 1, change "A protective covering" to --A glove--.

Claim 11, line 1, change "coating" to --covering--.

Signed and Sealed this

Thirteenth Day of September, 1994

Attest:

BRUCE LEHMAN

*Attesting Officer*       *Commissioner of Patents and Trademarks*